US006890308B2

(12) United States Patent
Islam

(10) Patent No.: US 6,890,308 B2
(45) Date of Patent: May 10, 2005

(54) BONE MARROW BIOPSY NEEDLE

(76) Inventor: Abul Bashar Mohammed Anwarul Islam, 3 Hardt La., Amherst, NY (US) 14226

( * ) Notice: Subject to any disclaimer, the term of this patent is extended or adjusted under 35 U.S.C. 154(b) by 0 days.

(21) Appl. No.: 10/453,094

(22) Filed: Jun. 3, 2003

(65) Prior Publication Data
US 2004/0249306 A1 Dec. 9, 2004

(51) Int. Cl.[7] .............................................. A61B 10/00
(52) U.S. Cl. ......................... 600/564; 600/567; 606/170
(58) Field of Search ........................ 600/562, 564–567, 600/573; 606/167, 170

(56) References Cited

U.S. PATENT DOCUMENTS

| 4,487,209 | A |   | 12/1984 | Mehl |         |
|-----------|---|---|---------|------|---------|
| 5,098,435 | A | * | 3/1992  | Stednitz et al. | 606/73 |
| 5,660,186 | A | * | 8/1997  | Bachir | 600/562 |
| 6,086,543 | A | * | 7/2000  | Anderson et al. | 600/567 |
| 6,620,111 | B2 | * | 9/2003 | Stephens et al. | 600/567 |
| 2002/0042581 | A1 | * | 4/2002 | Cervi | 600/567 |
| 2002/0188300 | A1 | * | 12/2002 | Arramon et al. | 606/93 |

FOREIGN PATENT DOCUMENTS

| GB | 1252170 | 11/1971 |
| GB | 2099703 A | 12/1982 |
| GB | 2130890 A | 6/1984 |
| WO | WO 96/27330 A1 | 9/1996 |

* cited by examiner

Primary Examiner—Charles Marmor
(74) Attorney, Agent, or Firm—Edwin D. Schindler

(57) ABSTRACT

A needle for use in taking a bone marrow biopsy comprises a hollow tube having a front end portion formed to a reduced diameter by swaging. The front end is tapered by means of a number of circumferentially-spaced facets, forming a cutting edge. A tapering transition portion, between the main portion of the hollow tube and its reduced-diameter front end portion, is formed with a series of flutes which help in the needle cutting through the cortical bone. A spacer is provided for use in pushing the sample rearwardly out of the hollow tube, the spacer having a through-passage through which a trocar needle is passed and serving for accurate alignment of the distal ends of the hollow tube and trocar needle.

9 Claims, 3 Drawing Sheets

BONE MARROW BIOPSY NEEDLE

FIELD OF THE INVENTION

The present invention relates to a biopsy needle for use in taking a bone marrow biopsy sample from a posterior iliac crest of a patient.

BACKGROUND OF THE INVENTION

U.S. Pat. No. 4,543,966 and UK patent No. 2,099,703 relate to a bone marrow biopsy needle assembly which comprises an elongate hollow needle having open front and rear ends, the front end being provided with a cutting edge: furthermore, a portion of the needle, adjacent its front end, is of a reduced internal diameter and an internal shoulder is formed between the inner end of this reduced-diameter portion and the WIDER main portion of the needle. The hollow needle is used with a trocar needle or stilette which is inserted into the hollow needle from its rear end, for a pointed front end of the trocar needle to project beyond the front end of the hollow needle.

In use, this assembly is gradually advanced, by hand, through the soft skin tissue and then through the cortical bone of the patient, by the execution of alternate clockwise and counterclockwise rotations of the assembly around its longitudinal axis. Once the assembly has advanced through the cortical bone, to reach the underlying spongy or medullary bone, the trocar needle or stilette is withdrawn from the hollow needle: then the hollow needle is advanced into the spongy bone, again by the execution of alternate clockwise and counterclockwise rotations or rotary motions of the hollow needle; it will be appreciated that a core sample of bone marrow will accordingly enter the hollow needle, from its front end. When the hollow needle has been advanced to a sufficient depth into the spongy bone, about 20 to 25 mm, the hollow needle is rotated several times about its longitudinal axis to sever all the trabecular connections at its base and break the core sample loose from the rest of the spongy bone, and is then withdrawn. The core sample of bone marrow is retained within the hollow needle and this retention is particularly facilitated by the internal step which acts as a shoulder and also because of the fact that the core sample expands in diameter in the wider portion of the needle, inwardly or to the rear of the front end portion of reduced internal diameter. The core sample is subsequently removed from the hollow needle by inserting an elongate pusher rod into the hollow needle from its front end.

The above-described biopsy needle assembly is effective in use but it is necessary to make the hollow needle by hand, in order to provide its front end portion of reduced diameter: the hollow needle is accordingly expensive to manufacture. Also, I have now devised a modification to the needle in order to improve its ability to advance through the cortical bone.

SUMMARY OF THE INVENTION

In accordance with the present invention, there is provided a needle for use in taking a bone marrow biopsy, the needle comprising a hollow tube having a main portion, a front end portion formed to a reduced diameter compared with said main portion, and a tapering portion disposed between said main portion and said front end portion, said tapering portion comprising a series of flutes spaced apart around its circumference.

The flutes, provided on the tapering portion of the hollow needle, serve for cutting the cortical bone, by alternate clockwise and counterclockwise rotations of the hollow needle, to allow the larger-diameter main portion of the needle to advance smoothly and without resistance through the cortical bone.

Also, in accordance with the present invention, there is provided a needle for use in taking a bone marrow biopsy, the needle comprising a hollow tube having a front end portion formed to a reduced diameter by swaging.

It will be appreciated that the above-defined hollow needle will be used with a trocar needle or stilette to form a biopsy needle assembly for use in taking a bone marrow biopsy. This biopsy needle assembly is used in the same manner as the assembly of the above-noted U.S. Pat. No. 4,543,966 and UK patent No. 2,099,703. However, the hollow needle does not have to be made by hand: the swaging process, to form the reduced-diameter front end portion of the hollow needle, may be carried out by machine and the hollow needle is therefore less expensive to manufacture.

Preferably a transverse and domed handle is mounted to the rear end of the hollow tube, a domed head or cap is mounted to the rear end of the trocar needle or stilette, and a spacer is disposed between the handle and the head of the trocar needle, the spacer being formed with a through-passage through which the trocar needle passes. The spacer is used when removing the core sample from the hollow needle: thus, the reduced diameter front end portion of the hollow needle is engaged into one end of the through-passage of the spacer; then the pointed front end of the trocar needle is inserted through the spacer passage from its opposite end, and into the end of the hollow tube. The trocar needle is advanced to push the sample out of the rear end of the hollow needle.

Also in accordance with the present invention, there is provided a method of forming a needle for use in taking a bone marrow biopsy, the method comprising providing a hollow tube and swaging a front end portion of the tube to a reduced diameter.

BRIEF DESCRIPTION OF THE DRAWINGS

An embodiment of the present invention will be described by way of example only and with reference to the accompanying drawings, in which.

DETAILED DESCRIPTION OF THE PREFERRED EMBODIMENT

Figure 1:
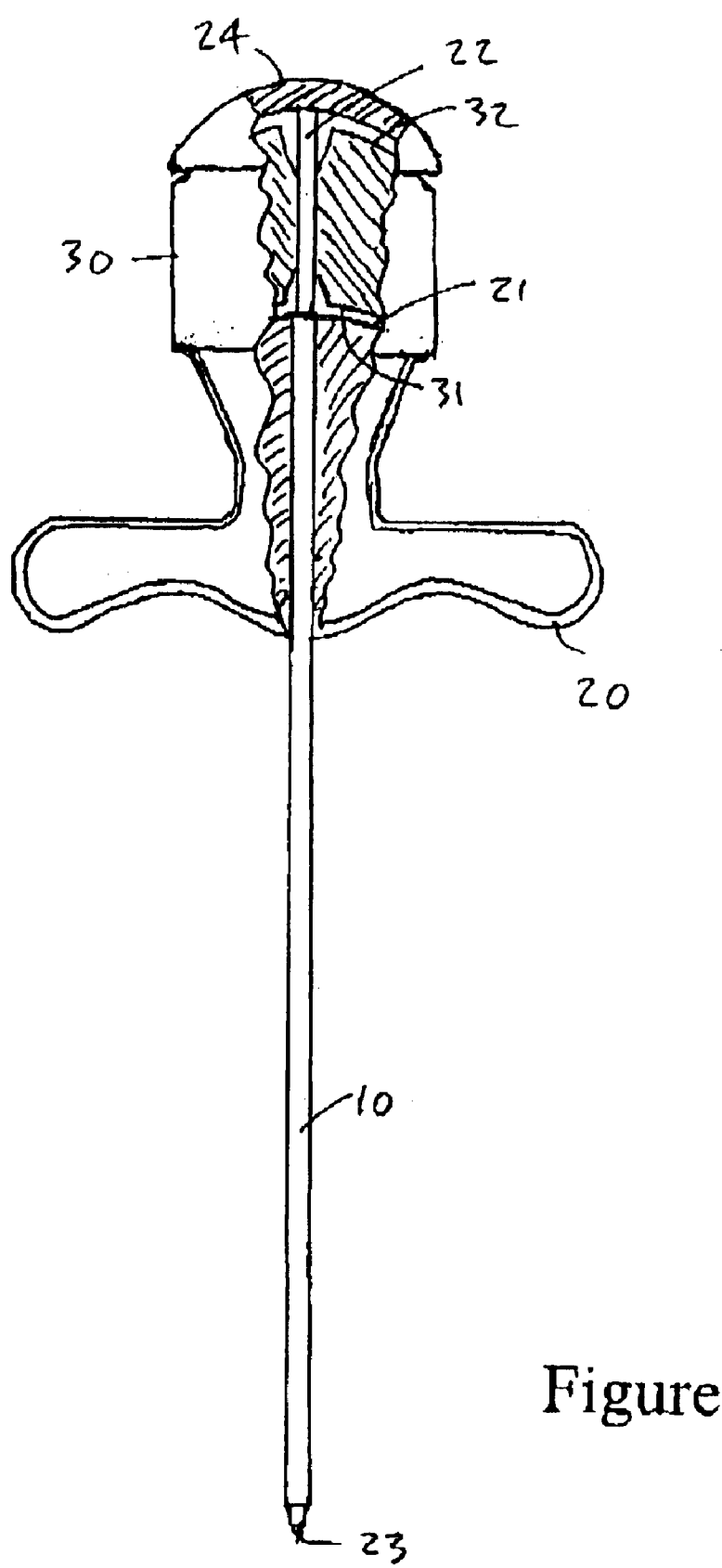
FIG. 1 is a side view, partly in section of a biopsy needle assembly in accordance with the present invention.

Referring to FIG. 1 of the drawings, there is shown a disposable needle assembly for taking a bone marrow biopsy sample. The assembly comprises a hollow needle 10, fitted, at its rear end, with a transverse handle 20 having a domed end 21: the assembly further comprises a trocar needle or stilette 22 having a pointed front end 23 and a domed head 24 at its rear end, the trocar needle 22 being shown inserted through a spacer 30 and through the hollow needle 10 for its pointed end 23 to project from the front end of the hollow needle 10. The spacer 30 has a concave-profiled lower end 31 to seat on the domed end 21 of the handle 20 of the hollow needle 10, and a convex-profiled upper end 32 for the underside of the head 24 of the trocar needle 22 to seat upon.

Figure 2:
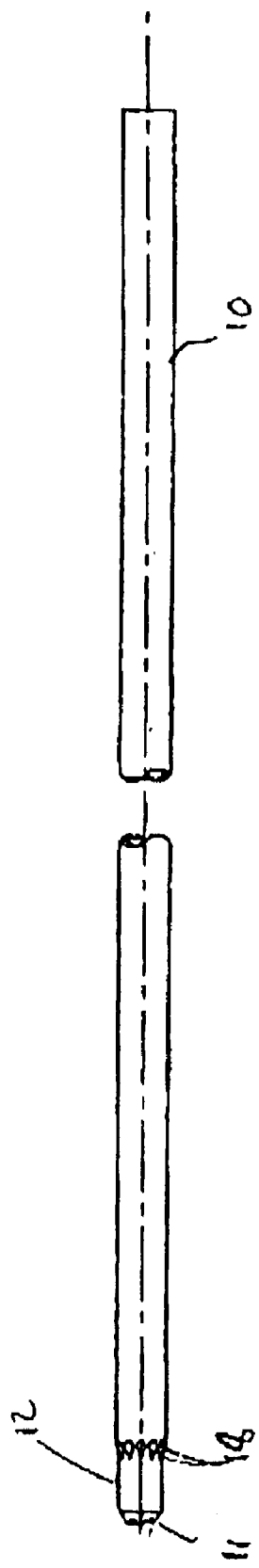
FIG. 2 is a side view of a hollow metal needle of the biopsy needle assembly, the hollow needle being shown without its handle and without the trocar needle or stilette of the assembly.
Figure 3:
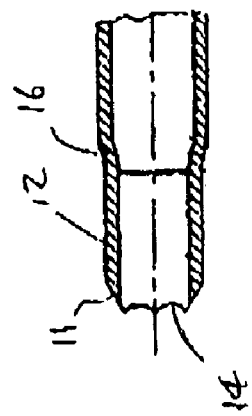
FIG. 3 is an enlarged longitudinal sectional view of the hollow needle adjacent its front end.
Figure 4:
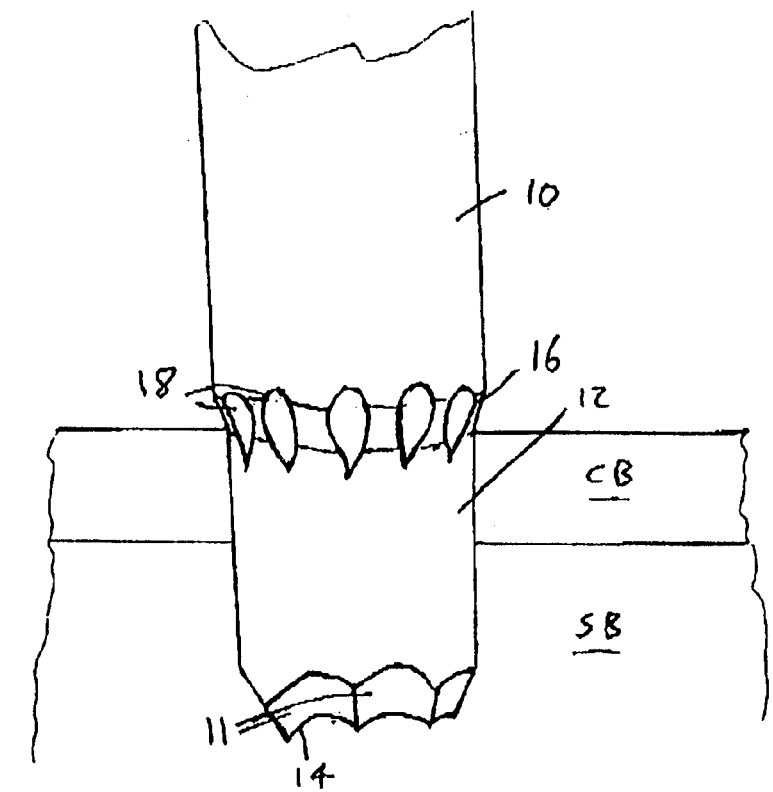
FIG. 4 is an enlarged view showing use of the hollow needle when taking a bone marrow biopsy.

Referring to FIGS. 2 and 3 of the drawings, the hollow needle 10 comprises a stainless steel tube of circular cross-section and uniform diameter, a front end portion 12 of which has been formed to a reduced diameter by swaging. The front end of the tube 10 is tapered by means of six equi-angularly spaced facets 11, thus forming a cutting edge 14. The swaging process, for forming the front end portion to its reduced diameter, results in the formation of a generally frustoconical transition portion 16 between the main portion of the tube 10 and the front end portion 12: the outer surface of this transition portion is formed with twelve equi-angularly spaced flutes 18. Typically, the tube 10 may have a uniform external diameter of 3.25 mm and a uniform internal diameter of 2.5 mm, except for the front end portion 12 which is typically 3.5 mm in length and has an internal diameter (e.g. of 2.1 mm) less than the internal diameter of the main portion of the tube.

The biopsy needle assembly of the present invention is used in the same manner as the assembly of the above-noted U.S. Pat. No. 4,543,966 and UK patent No. 2,09,703. When the assembly reaches the spongy bone (FIG. 3), the trocar needle 22 is withdrawn. The hollow needle 10 is then advanced further, the flutes 18 on the transitional portion 16 serving to cut through the cortical bone as the needle is turned alternatively clock-wise and anti-clockwise, to allow the larger-diameter main portion of the hollow needle 10 to pass through the cortical bone. When the hollow needle 10 has been advanced a sufficient depth into the spongy bone, the hollow needle 10 is rotated several times to cut all the trabecular connections and break the core sample loose from its base, and is then withdrawn. Using this device, the core sample is retained within the hollow needle 10, being embraced at its trailing end by the reduced-diameter front end portion of the hollow needle 10 the main portion of the hollow needle is of larger diameter, beyond the tapering transition between the main portion and front end portion, so that impaction, crushing and compres-sion of the core sample are prevented. As the core sample enters the wider main portion of the hollow tube 10, it expands slightly in diameter, helping to prevent it slipping out of the needle as the latter is withdrawn: the core sample remains free, however, to slide rearwardly along the main portion of the hollow tube when pushed out by the trocar needle, as described below.

Figure 5:
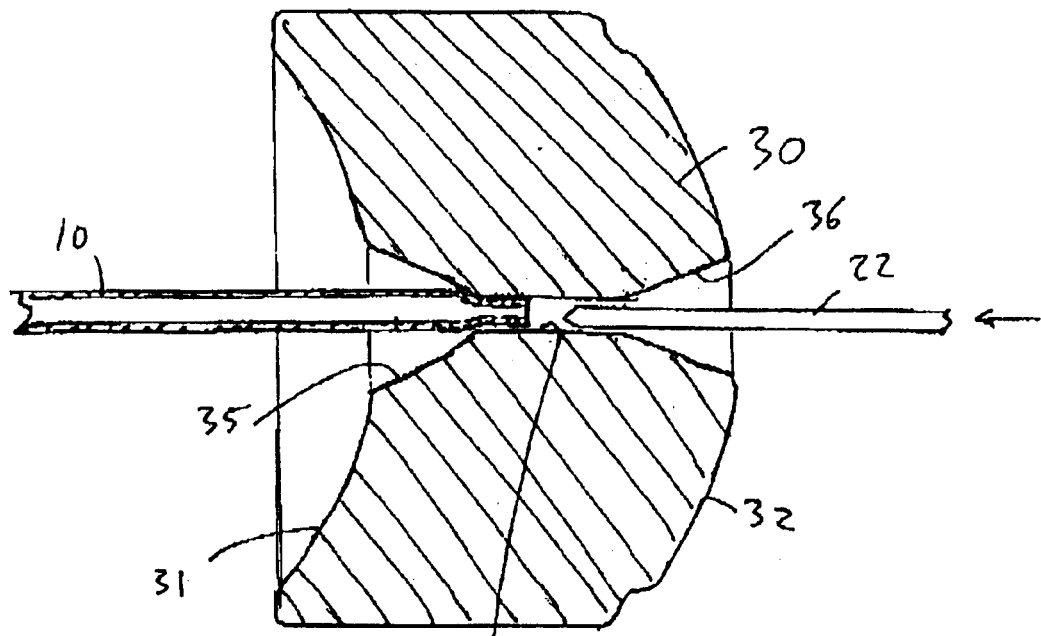
FIG. 5 is an enlarged view of a spacer member of the biopsy needle assembly, shown applied to the front end of the hollow needle after a biopsy sample has been taken, and with the front end of the trocar needle about to be inserted to push the sample out.

Referring to FIG. 5, the core sample is removed from the hollow needle in the following manner. The spacer 30 is applied to the forward end of the hollow needle 10, this end of the hollow needle 10 engaging into the lower end of a central bore 34 through the spacer. The pointed front end of the trocar needle or stilette 22 is then inserted through the spacer 30 from its upper end, and into the end of the hollow needle 10: the trocar needle 22 is advanced to push the sample out of the rear end of the hollow needle 10. It will be noted that the central bore 34 of the spacer is funnel-shaped at both its ends 35,36, to facilitate introduction of the ends of the hollow needle 10 and trocar needle 22. The spacer 30 accordingly forms an effective aid for alignment of the trocar needle 22 with, and its insertion into, the hollow needle 10.

In contrast to the biopsy needle of U.S. Pat. No. 4,543,966 and UK patent No. 2,099,703, the hollow needle 10 is not required to be made by hand: in particular, the swaging process, to form the reduced-diameter front end portion 12, may be carried out by machine; also, the tapering facets 11, to form the cutting edge 14, and the flutes 18 may all be formed by machine. The biopsy needle 10 is accordingly relatively easy to manufacture, less expensive and more importantly enabling a large number of such needles to be produced in a short time span, which is essential where the needles are intended for single-use.

What is claimed is:

1. A needle for taking a bone marrow biopsy, comprising:
   a hollow tube having a main portion and a front end portion, with said front end portion being of a reduced diameter, both internally and externally, when compared with said main portion, wherein a distal end of said front end portion, remote from said main portion, has a multifaceted cutting edge, and a proximal end of said front end portion, in proximity to said main portion, has a tapering portion formed by swaging for providing a frustoconical transition between said front end portion and said main portion with an outer surface of said frustoconical transition including a series of flutes circumferentially around said tapering portion, wherein each flute of said series of flutes has a recess in the outer surface of said frustoconical transition bounded by two cutting surfaces running, at least, part way along a longitudinal axis of said tapering portion, said series of flutes providing a further cutting surface in addition to said multifaceted cutting edge at said distal end of said front end portion.

2. The needle for taking a bone marrow biopsy according to claim 1, wherein said distal end of said front end portion of said hollow tube is tapered via a series of facets, spaced apart, circumferentially around said distal end of said hollow tube.

3. A biopsy needle assembly, comprising:
   a needle for taking a bone marrow biopsy, said needle comprising:
      a hollow tube having a main portion and a front end portion, with said front end portion being of a reduced diameter, both internally and externally, when compared with said main portion, wherein a distal end of said front end portion, remote from said main portion, has a multifaceted cutting edge, and a proximal end of said front end portion, in proximity to said main portion, has a tapering portion for providing a frustoconical transition between said front end portion and said main portion with an outer surface of said frustoconical transition including a series of flutes circumferentially around said tapering portion, wherein each flute of said series of flutes has a recess in the outer surface of said frustoconical transition bounded by two cutting surfaces running, at least, part way along a longitudinal axis of said tapering portion, said series of flutes providing a further cutting surface in addition to said multifaceted cutting edge at said distal end of said front end portion; and,
   a trocar needle inserted into said hollow tube of said needle from a rear end of said hollow tube, so that a pointed front end of said trocar needle projects from said front end portion of said hollow tube.

4. The biopsy needle assembly according to claim 3, further comprising:
   a handle mounted to said rear end of said hollow tube;

a head mounted to a rear end of said trocar needle; and, a spacer disposed between said handle and said head, said spacer having a through-passage through which said trocar needle passes.

5. The biopsy needle assembly according to claim 4, wherein said through-passage of said spacer has two ends and is funnel-shaped at each end of said two ends.

6. A biopsy needle assembly, comprising:

a needle for taking a bone marrow biopsy, said needle comprising:

a hollow tube having a main portion and a front end portion, with said front end portion being of a reduced diameter, both internally and externally, when compared with said main portion, wherein a distal end of said front end portion, remote from said main portion, has a multifaceted cutting edge, and a proximal end of said front end portion in proximity to said main portions, has a tapering portion formed by swaging for providing a frustoconical transition between said front end portion and said main portion with an outer surface of said frustoconical transition including a series of flutes circumferentially around said tapering portion, wherein each flute of said series of flutes has a recess in the outer surface of said frustoconical transition bounded by two cutting surfaces running, at least, part way along a longitudinal axis of said tapering portion, said series of flutes providing a further cutting surface in addition to said multi-faceted cutting edge at said distal end of said front end portion; and, a trocar needle inserted into said hollow tube of said needle from a rear end of said hollow tube, so that a pointed front end of said trocar needle projects from said front end portion of said hollow tube.

7. The biopsy needle assembly according to claim 6, further comprising:

a handle mounted to said rear end of said hollow tube;

a head mounted to a rear end of said trocar needle; and, a spacer disposed between said handle and said head, said spacer having a through-passage through which said trocar needle passes.

8. The biopsy needle assembly according to claim 7, wherein said through-passage of said spacer has two ends and is funnel-shaped at each end of said two ends.

9. A method of forming a needle for taking a bone marrow biopsy, comprising the steps of:

providing a hollow tube;

swaging a front end portion of said hollow tube to a reduced diameter, internally and externally, over a length of said front end portion for forming a frustoconical transition between said front end portion and an adjacent portion of said hollow tube;

forming a series of flutes, spaced apart, circumferentially around said hollow tube in an outer surface of said frustoconical transition of said hollow tube such that said series of flutes forms a first cutting surface of the needle; and, tapering said front end portion of said hollow tube by forming a series of facets in an outer surface of said hollow tube, spaced apart, circumferentially around said hollow tube such that said series of facets forms a second cutting surface of the needle.

\* \* \* \* \*